United States Patent

King

Patent Number: 5,124,330
Date of Patent: Jun. 23, 1992

[54] (E)-ETHYL 3-(4-CHLORO-α-(4-METHYL-1-PIPERAZINYL)BENZYL)CINNAMATE USED FOR POTENTIATING THE EFFECTS OF ANTITUMOR AGENTS AND COMBATING MULTIPLE DRUG RESISTANCE

[75] Inventor: Ann C. King, Chapel Hill, N.C.

[73] Assignee: Burroughs Wellcome Company, Raleigh, N.C.

[21] Appl. No.: 539,836

[22] Filed: Jun. 18, 1990

[30] Foreign Application Priority Data

Jun. 19, 1989 [GB] United Kingdom ............... 8914040

[51] Int. Cl.⁵ .................. A01N 43/60; A61K 31/495
[52] U.S. Cl. .................................... 514/250; 514/255
[58] Field of Search ........................ 514/283, 255, 250

[56] References Cited

U.S. PATENT DOCUMENTS 3,996,222 12/1976 Kajfez et al. ............... 260/247.5 D
4,628,047 12/1986 Sakurai et al. ........................ 514/34
4,757,074 7/1988 Coker et al. ......................... 514/255
4,990,538 2/1991 Harris et al. ......................... 514/648

FOREIGN PATENT DOCUMENTS 0187700 7/1986 European Pat. Off. .
0353962 7/1989 European Pat. Off. .
0361485 9/1989 European Pat. Off. .
2120941A 12/1983 United Kingdom .

OTHER PUBLICATIONS

Wilson, C. M. et al., "Amplification of a Gene Related to Mammalian mdr Genes in Drug-Resistant Plasmodium falciparum," Science 244, 1184 (1989).
"The Merck Index," p. Misc-2 (11th Ed. 1989).

Primary Examiner—Nathan M. Nutter
Attorney, Agent, or Firm—Bell, Seltzer, Park & Gibson

[57] ABSTRACT

Potentiating agents which enhance the efficacy of antineoplastic agents are disclosed. The potentiating agents disclosed are piperazinyl benzyl compounds such as 1-[α-(4-chlorophenyl)-3-methoxybenzyl]-4-allylpiperazine dihydrochloride.

10 Claims, No Drawings

(E)-ETHYL 3-(4-CHLORO-α-(4-METHYL-1-PIPERAZINYL)-BENZYL)CINNAMATE USED FOR POTENTIATING THE EFFECTS OF ANTITUMOR AGENTS AND COMBATING MULTIPLE DRUG RESISTANCE

FIELD OF THE INVENTION

The present invention relates to the use of piperazinyl benzyl compounds as adjuvant chemotherapy for neoplasias resistant to multiple drugs. The present invention also relates to the use of such compounds as an agent for enhancing the therapeutic effect of multiple antitumor agents.

BACKGROUND OF THE INVENTION

Complete cures of various tumors like leukemias, lymphomas and solid tumors by the use of chemotherapeutic agents are rare because of heterogeneous sensitivity of tumor cells to each antitumor agent. Cancer chemotherapy also fails because of intrinsic resistance of tumors to multiple drug therapies. In other cases, a tumor may become resistant to the antitumor agents used in a previous treatment. The therapeutic effects of these agents are then eliminated. An even graver problem is that recurrent cancers are resistant not only to the cancer suppressants used in previous treatments, but also manifest resistance to other antitumor agents, unrelated to the agent used previously either by chemical structure or by mechanism of action. These phenomena are collectively referred to multiple drug resistance (mdr) and contribute widely to cancer treatment failures in the clinic.

The major documented cause of multiple drug resistance is overexpression of a membrane glycoprotein (the multiple drug transporter) responsible for pumping structurally diverse antitumor drugs from cells. See D. Houseman et al., *A Molecular Genetic Approach to the Problem of Drug Resistance in Chemotherapy,* 504–517 (1987) (Academic Press, Inc.); R. Fine and B. Chabner, *Multidrug Resistance, in Cancer Chemotherapy,* 117–128 (H. Pinedo and B. Chabner eds. 1986).

Tumor cells expressing elevated levels of the multiple drug transporter accumulate far less antitumor agents intracellularly than tumor cells having low levels of this enzyme. The degree of resistance of certain tumor cells has been documented to correlate with both elevated expression of the drug transporter and reduced accumulation of antitumor drugs. See M. Gottesman and I. Pastan, *J. Biol. Chem.* 263, 12163 (1988); see also A. Fojo et al., *Cancer Res.* 45, 3002 (1985). This form of multiple drug cross-resistance involves agents derived from natural products, such as the vinca alkaloids, the anthracyclines, the epipodophyllotoxins, actinomycin D and plicamycin. See I. Pastan and M. Gottesman, *New England J. Med.* 1388, 1389 Table 1 (May 28, 1987).

Adenocarcinomas derived from adrenal, kidney, liver, small intestine, and colon tissue are notorious for exhibiting inherent cross-resistance to chemically unrelated chemotherapeutic agents. See M. Gottesman and I. Pastan, supra at 12165; see also A. Fojo et al., *J. Clin. Oncol.* 5, 1922 (1987). These tissues normally express higher levels of the multidrug transporter. Other tumors documented to express high levels of the multidrug transporter include pancreatic, carcinoid, chronic myelogenous leukemia in blast crisis, and non-small cell lung carcinoma. Tumors documented to initially be drug-sensitive but to then become drug resistant include neuroblastoma, pheochromocytoma, acute lymphocytic leukemia in adults, acute nonlymphocytic leukemia in adults, nodular poorly differentiated lymphoma, breast cancer and ovarian cancers. It is estimated by the National Cancer Institute that approximately half a million tumor samples a year will be drug resistant because of aberrant levels of expression of the multidrug transporter. See L. Goldstein et al., Expression of Multidrug Resistance Gene in Human Cancers, *J. National Cancer Institute* 81. 116 (1988).

Elevated levels of expression of the mdr drug transporter in these tumors would lead to reduced intracellular levels of antitumor agents in the tumor and would cause suppression of chemotherapeutic efficacy. Tumors having elevated levels of the multiple drug transporter would require therapeutic doses of cancer suppressants far in excess of tumors exhibiting lower levels of the mdr drug transporter. Agents that inhibit the active efflux of antitumor agents by the drug transporter or agents that potentiate the efficacy of chemotherapeutic agents would enhance the activity of various antitumor agents on tumor cells. As a result of the present inventor's study, it has unexpectedly been found that when the potentiating agents disclosed herein are used together with an antitumor agent, they can remarkably enhance the therapeutic effect of the antitumor agent, and that multiple drug resistance is resolved by increasing the susceptibility to actinomycin D.

A number of agents used clinically as calcium channel-blockers, calmodulin inhibitors and antiarrhythmic agents promote the activity of antitumor agents against resistant tumor cells, see Tsuruo et al., *Cancer Res.* 44, 4303 (1984); , 43, 2267 (1983). Verapamil, caroverine, clomipramine, trifluoperazine, prenylamine, diltiazem, nicardipine, and quinidine enhance the activity of antitumor agents against resistant sublines of murine leukemia cells. Most agents potentiating the activity of antitumor agents are calcium antagonists, and the serious cardiotoxicities that arise during treatment have limited their clinical usefulness. While the inventor does not wish to be bound by any theory of operation for the present invention, it is noted that the potentiating agents disclosed herein are not known to have calcium antagonism, but do elevate the intracellular concentration of antineoplastic drugs in tumor cells overexpressing the multiple drug transporter. Sensitization of drug resistant tumors and elevation of intracellular antitumor drug concentrations probably occur by a mechanism different from calcium antagonism.

SUMMARY OF THE INVENTION

An object of the present invention is to provide an agent for enhancing the therapeutic effect of an antineoplastic agent by administering to a subject harboring a tumor a compound of Formula (I) below or a pharmaceutically acceptable salt thereof (hereafter referred to as the "potentiating agent")

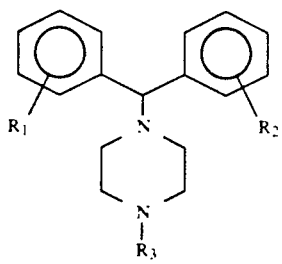

Wherein

R₁ can be halogen (e.g., chlorine or bromine);

R₂ can be hydrogen, halogen (e.g., chlorine, bromine), $C_{1-4}$ alkoxy (e.g., —OCH₃), —OCH₂C₆H₅, or —CH=CHCO₂R, wherein R is $C_{1-4}$ alkyl, preferably ethyl; and R₃ can be $C_{1-4}$ alkyl (e.g., —CH₃), —CH₂CH=CH₂, or —CH₂C₆H₄CH₃.

Another aspect of the present invention is a method of increasing the sensitivity of a tumor to an antineoplastic agent when the tumor is resistant to the antineoplastic agent by administering to the subject harboring the resistant tumor a potentiating agent concurrently with an antineoplastic agent. Resistance to the antineoplastic agent may (a) be an intrinsic property of the tumor or (b) develop in response to prior treatment with the same antineoplastic agent or another antineoplastic agent capable of selecting for multi-drug resistance.

Another aspect of the present invention is a method of selectively inhibiting the growth of tumor cells in a subject in need of such treatment by concurrently administering to the subject an antineoplastic agent and a potentiating agent. The potentiating agent is administered in an amount effective to (a) reduce the amount of the antineoplastic agent required to achieve the same growth inhibiting effect on the tumor cells by the antineoplastic agent achieved without the concurrent administration of the potentiating agent; or (b) inhibit the development of multiple drug resistance in the tumor cells after treatment with the antineoplastic agent over time. Another aspect of the present invention is a method of inhibiting multiple drug resistance in a subject in need of such treatment by administering the subject a potentiating agent in an amount effective to combat multiple drug resistance.

Also disclosed is the use of the compounds of Formula (I) above for the manufacture of a medicament for the inhibition of multiple drug resistance in tumors.

DETAILED DESCRIPTION OF THE INVENTION

Potentiating agents exemplary of the present invention include:

(A) 1-(3-Bromo-4'-chlorobenzhydryl)-4-methylpiperazine dihydrochloride;

(B) (E)-Ethyl 3-(4-chloro-α-(4-methyl-1-piperazinyl)-benzyl)cinnamate dihydrochloride;

(C) 1-(3-Benzyloxy-4'-chlorobenzhydryl)-4-methylpiperazine dihydrochloride;

(D) 1-(3-Benzyloxy-4'-chlorobenzhydryl)-4-(3-methylbenzyl)piperazine dihydrochloride;

(E) 1-(2-Bromo-4'-chlorobenzhydryl)-4-methylpiperazine dihydrochloride;

(F) 1-(α-(4-Bromophenyl)-3-methoxybenzyl)-4-methylpiperazine dihydrochloride; and (G) 1-[α-(4-Chlorophenyl)-3-methoxybenzyl]-4-allyl-piperazine dihydrochloride.

A preferred category of multiple drug resistant tumor cells to be treated by the method of the present invention are multiple drug resistant cells characterized by the multidrug transporter—mediated pumping of antineoplastic agents out of the tumor cells. The multidrug transporter protein is described in M. Gottesman and I. Pastan, supra. Thus, tumor cells treated by the present invention are preferably those characterized by (a) the expression of the multidrug transporter protein at high levels, or (b) the ability to express the multidrug transporter protein upon selection by an antineoplastic agent.

Exemplary of tumor cells which express the multidrug transporter at high levels (intrinsically resistant cells) are adenocarcinoma cells, pancreatic tumor cells, carcinoid tumor cells, chronic myelogenous leukemia cells in blast crisis, and non-small cell lung carcinoma cells.

Exemplary of tumor cells having the ability to express the multidrug transporter protein upon selection by an antineoplastic agent are neuroblastoma cells, pheochromocytoma cells, adult acute lymphocytic leukemia cells, adult acute nonlymphocytic leukemia cells, nodular poorly differentiated lymphoma cells, breast cancer cells and ovarian cancer cells.

A preferred group of tumor cells for treatment in the present invention are the adenocarcinomas, including adenocarcinomas of adrenal, kidney, liver, small intestine and colon tissue, with kidney adenocarcinoma cells particularly preferred.

Preferred antineoplastic agents for use in the present invention are those to which multidrug transporter—mediated multiple drug resistant cells develop resistance. Exemplary of such antineoplastic agents are vinca alkaloids, epipodophyllotoxins, anthracycline antibiotics, actinomycin D, plicamycin, puromycin, gramicidin D, taxol, colchicine, cytochalasin B, emetine, maytansine, and amsacrine (or "mAMSA"). Preferred are vinca alkaloids, epipodophyllotoxins, anthracyclene antibiotics, actinomycin D, and plicamycin.

The vinca alkaloid class is described in *Goodman and Gilman's The Pharmacolooical Basis of Therapeutics*, 1277–1280 (7th ed. 1985) (hereafter "Goodman and Gilman"). Exemplary of vinca alkaloids are vincristine, vinblastine, and vindesine.

The epipodophyllotoxin class is described in Goodman and Gilman, supra at 1280–1281. Exemplary of epipodophyllotoxins are etoposide, etoposide orthoquinone, and teniposide.

The anthracycline antibiotic class is described in Goodman and Gilman, supra at 1283–1285. Exemplary of anthracycline antibiotics are daunorubicin, doxorubicin, mitoxantraone, and bisanthrene. Daunorubicin and doxorubicin are preferred.

Actinomycin D, also called Dactinomycin, is described in Goodman and Gilman, supra at 1281–1283. Plicamycin, also called mithramycin, is described in Goodman and Gilman, supra at 1287–1288.

The phrase "concurrently administering," as used herein, means that the antineoplastic agent and the potentiating agent are administered either (a) simultaneously in time (optionally by formulating the two together in a common carrier), or (b) at different times during the course of a common treatment schedule. In the latter case, the two compounds are administered at times sufficiently close for the potentiating agent to enhance the selective growth-inhibiting action of the antineoplastic agent on the tumor cells.

Subjects to be treated by the method of the present invention include both human and animal (e.g., dog, cat, cow, horse) subjects, and are preferably mammalian subjects.

The potentiating agent is administered in an amount effective to enhance the efficacy of the antineoplastic agent. The potentiating agent is preferably administered in a total amount per day of not more than about 50 mg/kg body weight, more preferably not more than about 25 mg/kg, and most preferably not more than about 5 mg/kg. With respect to minimum dose, the potentiating agent is preferably administered in a total amount per day of at least about 0.01 mg/kg, more preferably at least about 0.1 mg/kg, and most preferably at least about 1 mg/kg. The potentiating agent may be administered once or several times a day.

As noted above, the compounds of Formula (I) may be administered per se or in the form of a pharmaceutically acceptable salt. When used in medicine, the salts of the compounds of Formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, isethionic, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise the potentiating agent together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

Pharmaceutical formulations of the present invention may optionally include an antineoplastic agent, preferably an agent as described above. Such a formulation is useful for concurrently administering an antineoplastic agent and the potentiating agent in a method as described above.

The formulations include those suitable for oral, rectal, topical, nasal, ophthalmic or parenteral (including subcutaneous, intramuscular and intravenous) administration. Formulations suitable for oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the potentiating agent as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The following Examples are provided to illustrate the present invention, and should not be construed as limiting thereof. Temperatures are given in degrees Celsius unless otherwise indicated.

EXAMPLE 1

(E)-Ethyl 3-(4-chloro-α-(4-methyl-1-piperazinyl)benzyl)cinnamate (Compound B)

1-(3-Bromo-4'-chlorobenzhydryl)-4-methylpiperazine (see U.S. Pat. No. 4,757,074) (1.00 g, 2.63 mmole) was dissolved in 12 ml of dry tetrahydrofuran under nitrogen and cooled to −78° C. A solution of 1.1 M n-butyllithium in hexane (2.4 ml) was added dropwise and the reaction was stirred for ten minutes. N,N-Dimethylformamide (0.25 ml, 3.2 mmole) was added in one portion and the reaction was allowed to warm to −40° C. Hydrochloric acid (1.0 M, 20 ml) was added and the reaction was warmed to room temperature. The solution was washed with 20 ml of diethyl ether and the ethereal wash was discarded. The aqueous solution was made basic with aqueous sodium hydroxide and extracted with two 15 ml portions of chloroform. The combined chloroform extracts were dried over sodium sulfate and the solvent removed to give 738 mg of crude 1-(4-chloro-3'-formylbenzhydryl)-4-methylpiperazine as a dark oil.

Triethylphosphonoacetate (0.59 ml, 3.0 mmole) was added dropwise to a flask containing 50% sodium hydride dispersion in oil (128 mg, 2.7 mmole) and 3.5 ml of dry tetrahydrofuran under nitrogen. The reaction was stirred at room temperature for 15 minutes or until hydrogen evolution ceased. The 738 mg of crude aldehyde from above (approximately 2.2 mmole) was dissolved in 9 ml of dry tetrahydrofuran and added to the reaction. After stirring overnight at room temperature, the reaction was diluted with 15 ml of 1.0 M hydrochloric acid and washed with 20 ml of diethyl ether. The aqueous layer was made basic with aqueous sodium hydroxide and extracted with two 15 ml portions of chloroform. The combined chloroform extracts were dried over sodium sulfate and the solvent was removed to give 890 mg of crude cinnamate ester which was purified by silica gel chromatography (Waters Prep 500) with dichloromethane/ethanol/triethylamine (100:0.5:0.1) to give 560 mg of an oil. The product was converted to the dihydrochloride salt with ethanolic hydrochloric acid and the salt was crystallized from diethyl ether to give a hygroscopic white salt. Drying under vacuum gave 412 mg (32% overall) of (E)-ethyl 3-(4-chloro-α-(4-methyl-1-piperazinyl)benzyl)cinnamate as white crystals, mp. 165°–172° C., calc. for $C_{23}H_{27}ClN_2O_2$ 2HCl $H_2O$: C, 56.39; H, 6.38; N, 5.72; Cl, 21.71. Found: C, 56.40; H, 6.39; N, 5.72; Cl, 21.67.

EXAMPLE 2

1-(3-Benzyloxy-4'-chlorobenzhydryl)-4-(3-methylbenzyl)piperazine (Compound D)

α-Bromo-m-xylene (10 ml, 74 mmole) was added to a solution of 75 g (11.8 equiv.) of anhydrous piperazine in 500 ml of benzene and the reaction was heated to reflux for two hours. After cooling to room temperature, the reaction was diluted with 300 ml of diethyl ether and washed with 500 ml of 0.2 M sodium hydroxide followed by two 500 ml portions of water. The organic solution was dried over sodium sulfate and the solvent removed to give 11.0 g (78%) of crude 1-(3-methylbenzyl)piperazine as a colorless oil.

The crude piperazine derivative from above (11.0 g, 56 mmole) was dissolved in 150 ml of toluene and added to 19.2 g (56 mmole) of 3-benzyloxy-4'-chlorobenzhydryl chloride (see U.S. Pat. No. 4,757,074) and heated to reflux for 40 hours. The reaction was cooled to room temperature, diluted to 600 ml with diethyl ether, and washed with 100 ml of 1.0 M sodium hydroxide followed by three 200 ml portions of water and 100 ml of saturated sodium chloride. The product was dried over sodium sulfate and the solvent removed to give 27.0 g of crude product as a dark oil. The material was purified by chromatography on silica gel (Waters Prep 500) with 0.1% triethylamine in dichloromethane to give 14.7 g (53%) of 1-(3-benzyloxy-4'-chlorobenzhydryl)-4-(3-methylbenzyl) piperazine as a dark oil. A 5.0 g portion of the oil was dissolved in 00 ml of 2:1 ethanol:methanol and treated with an excess of ethanolic hydrochloric acid to produce the dihydrochloride salt of the product. Addition of 150 ml diethyl ether and cooling provided 1.74 g of the salt as white crystals, mp. 204°–208° C. Calc. for $C_{32}H_{33}ClN_2O$ 2HCl: C, 67.43; H, 6.19; N, 4.91; Cl, 18.66. Found: C, 67.15; H, 6.14; N, 4.87; Cl, 18.58.

EXAMPLE 3

1-(α-(4-Bromophenyl)-3-methoxybenzyl)-4-methylpiperazine (Compound F)

p-Dibromobenzene (7.08 g, 30.0 mmole) was added to 50 ml of anhydrous tetrahydrofuran under nitrogen and the slurry was cooled to −78° C. A solution of n-butyllithium in hexane (1.67 M, 18.0 ml, 30 mmole) was added dropwise over 15 minutes. After stirring for ten minutes at −78° C., 3.8 ml (4.1 g, 30 mmole) of m-anisaldehyde was added dropwise over five minutes. After stirring for 15 minutes, the reaction was quenched with 10 ml of saturated aqueous ammonium chloride solution and was allowed to warm to room temperature. The reaction solution was diluted with 300 ml of diethyl ether and washed with three 50 ml portions of 1.0 M aqueous sodium bisulfite, followed by 50 ml of 1.0 M sodium hydroxide, 100 ml of water, and 100 ml of saturated sodium chloride. After drying over magnesium sulfate, the solvent was removed to give 8.5 g (97%) of crude (4-bromophenyl)(3-methoxyphenyl)-methanol.

The crude alcohol from above (6.5 g, 22 mmole) was dissolved in 50 ml of dichloromethane, and 2.4 ml (33 mmole) of thionyl chloride was added dropwise at room temperature. The reaction was allowed to stir overnight and the solvent was removed under vacuum. The crude product was redissolved in 50 ml of toluene and the solvent was again removed under vacuum in order to eliminate excess thionyl chloride, providing 6.85 g of crude 4-bromo-3'-methoxybenzhydryl chloride as a dark oil.

The crude benzhydryl chloride from above (6.5 g, 21 mmole) was added to 8.3 g (83 mmole) of 1-methylpiperazine and the reaction was heated to reflux for four hours. After cooling to room temperature, the mixture was dissolved in 100 ml of ethyl acetate and washed with two 150 ml portions of 1.0 M sodium hydroxide, followed by two 150 ml portions of water and 100 ml of saturated aqueous sodium chloride. The solution was dried over magnesium sulfate and the solvent removed to give 6.5 g of crude product as an oil. The product was purified by chromatography on silica gel (Waters Prep 500) with dichloromethane:ethanol:triethylamine (100:0.2:0.1) to give a colorless oil. A portion was converted to the dihydrochloride salt with ethanolic hydrochloric acid and precipitated from ethanol with 1:1 hexane:diethyl ether to give 1-(α-(4-bromophenyl)-3-methoxybenzyl)-4-methylpiperazine dihydrochloride as a white powdery solid, mp. 195°–197° C. Calc. for $C_{19}H_{23}BrN_2O$ 2HCl: C, 50.91; H, 5.62; N, 6.25; Total halogen calc. as Cl, 23.73. Found: C, 51.00; H, 5.66; N, 6.23; Total halogen calc. as Cl, 23.78.

EXAMPLE 4

1-(2-Bromo-4'-chlorobenzhydryl)-4-methylpiperazine (Compound E)

A solution of 23.0 g (120 mmole) of 4-bromochlorobenzene in 150 ml of dry tetrahydrofuran was cooled to −78° C. under nitrogen and 78 ml (120 mmole) of 1.55 M n-butyllithium in hexane was added dropwise at a rate to maintain temperature below −60° C. After stirring an additional 15 minutes, 14.0 ml (120 mmole) of 2-bromo-benzaldehyde was added and the reaction was stirred for 15 minutes. The reaction was quenched at −78° C. with saturated aqueous ammonium chloride and allowed to warm to room temperature. The reaction solution was diluted with 300 ml of diethyl ether and washed with three 75 ml portions of 1.0 M sodium bisulfite, followed by 50 ml of 1.0 M sodium hydroxide, 100 ml of water, and 50 ml of saturated sodium chloride. After drying over magnesium sulfate, the solvent was removed to give 35.3 g (99%) of crude 2-bromo-α-(4-chlorophenyl)benzyl alcohol as a pale yellow oil.

The crude benzhydryl alcohol from above (31.8 g, 107 mmole) was dissolved in 150 ml of dichloromethane and 11.7 ml (1.5 equiv.) of thionyl chloride was added dropwise over ten minutes. The solution was stirred overnight at room temperature and the solvent was removed under vacuum. The crude product was redissolved in 100 ml of toluene and the solvent was again removed under vacuum in order to eliminate excess thionyl chloride, providing crude product as a dark oil. The material was purified by short path distillation (Kugelrohr apparatus, 150° C., 0.5 mm) to give 25.8 g (76%) of (2-bromophenyl)chloro(4-chlorophenyl)methane as a pale yellow oil.

The crude benzhydryl chloride from above (22.5 g, 71 mmole) was added to 32 ml (4 equiv.) of 1-methylpiperazine and heated at 150° C. for 20 hours. After cooling to room temperature, the reaction mixture was dissolved in 250 ml of dichloromethane and washed with 20 ml of 1.0 M sodium hydroxide and four 250 ml portions of water. The organic solution was dried with sodium sulfate and the solvent removed to give a black oil. The oil was redissolved in 200 ml of diethyl ether with 100 ml of 1.0 M hydrochloric acid. The layers were separated and the ether layer was extracted with another 100 ml of 0.01 M hydrochloric acid. Combined aqueous layers were made basic with 1.0 M sodium hydroxide and extracted with three 100 ml portions of dichloromethane. The combined dichloromethane extracts were dried over sodium sulfate and the solvent removed to give 13.5 g (50%) of a pale yellow oil. A portion (8.8 g) of the oil was converted to the dihydrochloride salt with excess ethanolic hydrochloric acid and precipitated from ethanol with diethyl ether to give 6.88 g of 1-(2-bromo-4'-chlorobenzhydryl)-4-methylpiperazine dihydrochloride as a white powdery solid, mp. 229°–231° C. Calc. for $C_{18}H_{20}BrClN_2$ 2HCl: C, 47.76; H, 4.90; N, 6.19; Total halogen calc. as Cl, 31.33. Found: C, 47.80; H, 4.92; N, 6.17; Total halogen calc. as Cl, 31.32.

EXAMPLE 5

1-(α-(4-Chlorophenyl)-3-methoxybenzyl)-4-allylpiperazine (Compound G)

A solution of 35.0 g (183 mmole) of 4-bromochlorobenzene in 300 ml of dry tetrahydrofuran was cooled to −78° C. under nitrogen and 115 ml (183 mmole) of 1.59 M n-butyllithium in hexane was added dropwise at a rate to maintain temperature below −60° C. After stirring an additional 15 minutes, 23.0 ml (183 mmole) of m-anisaldehyde was added dropwise and the reaction was stirred for 15 minutes. The reaction was quenched at −78° C. with saturated aqueous ammonium chloride and allowed to warm to room temperature. The reaction solution was diluted with 300 ml of diethyl ether and washed with three 150 ml portions of 1.0 M sodium bisulfite, followed by 100 ml of 1.0 M sodium hydroxide, 100 ml of water, and 50 ml of saturated sodium chloride. After drying over magnesium sulfate, the solvent was removed to give 45.2 g (99%) of crude 4-chloro-α-(3-methoxyphenyl)benzyl alcohol as a pale yellow oil.

The crude benzhydryl alcohol from above (45.2 g, 182 mmole) was dissolved in 400 ml of dichloromethane and 16 ml (1.2 equiv.) of thionyl chloride in 100 ml of dichloromethane was added dropwise. The solution was stirred overnight at room temperature and the solvent was removed under vacuum. The crude product was redissolved in 200 ml of toluene and the solvent was again removed under vacuum in order to eliminate excess thionyl chloride, providing crude product as a dark oil.

The crude benzhydryl chloride from above (approx. 48 g, 180 mmole) was dissolved in 200 ml of toluene with 23 g (1 equiv.) of N-allylpiperazine and the bulk of the toluene was removed under vacuum. Tetramethylethylenediamine (30 ml, approx. 1.1 equiv.) was added to the mixture and the resulting reaction was heated at reflux for 20 hours under nitrogen. The remaining solvent was removed under vacuum. The residue was dissolved in 500 ml of dichloromethane and washed with 250 ml of 1.0 M sodium hydroxide, followed by three 500 ml portions of water. After drying over sodium sulfate, the solvent was removed to give 59.7 g of dark oil. The material was purified by chromatography on silica gel (Waters Prep. 500) with 0.1% triethylamine in dichloromethane to give 28.97 g (45%) of dark oil. The product was converted to its dihydrochloride salt with excess ethanolic hydrochloric acid and precipitated from ethanol with 1:1 hexane:diethyl ether to give 27.6 g of 1-(α-(4-chlorophenyl)-3-methoxybenzyl)-4-allylpiperazine dihydrochloride as a white powder, mp. 215°–218° C. Calc. for $C_{21}H_{25}ClN_2O$ 2HCl: C, 58.68; H, 6.33; N, 6.52; Cl, 24.75. Found: C, 58.49; H, 6.37; N, 6.46; Cl, 24.68.

EXAMPLE 6

In Vitro Cytotoxicity of Potentiating Agents in Chinese Hamster Ovary Cells

Chinese hamster ovary (CHO) tissue culture cells were obtained from Dr. Vic Ling, Princess Margaret Hospital, Toronto, Canada. The parental cell line (AuxB1) and a multidrug resistant line (C5S32) having an amplified form of the MDR drug transport protein were plated into 96-well microtitre culture dishes at 250 or 500 cells per well in minimal essential medium, type alpha, 10% fetal calf serum and incubated in 95% oxygen/5% carbon dioxide for 48 hours. After this period, the medium was changed and one-half of the culture was treated with Actinomycin D (Act D) (0.0μM for AuxB1 cells and 0.5 μM for C5S32 cells). C5S32 cells are about 200-fold resistant to Actinomycin D compared to the parental AuxB1 cell line. In addition to Act D some of the cultures also received a dose of the potentiating agent at 1 and 10 μM. Thus, four conditions were tested in each screening assay: untreated cells in medium alone, cells receiving Act D alone, cells incubated with the potentiating agent alone, and cells incubated with a combination of Act D and the potentiating agent. Both the parental and mdr cell lines were treated with these four conditions simultaneously. Each experimental condition reported below is based on the average absorbance from eight replicate samples. The incubation with Act D and the test drug continued for 96 additional hours, after which 0.5 mg/ml MTT dye was added to the cultures and allowed to incubate for three hours. The cells were solubilized by addition of DMSO and the absorbance at 570 nm was monitored. The absorbance is directly related to the number of surviving cells in the culture dish.

In Table 1 below, the absorbance was normalized so that cytotoxicity of the potentiating agent could be evaluated. Untreated cultures were given a value of 1.00 and the cultures receiving 1 and 10 μM of the potentiating agent are reported as a fraction of this value. To evaluate the compounds for inducing synergism with Actinomycin D, the absorbance values of cultures receiving Act D alone were assigned a value of 1.00 and cultures receiving the combination of Act D and potentiating agent Act D are reported as a fraction of this control. In most experiments, this concentration of Act D gave a reduction in cell number 10–20% below the value of completely untreated cultures.

TABLE 1

In Vitro Cytotoxicity of Potentiating Agents in Chinese Hamster Ovary Cells

| Compound | Dose | Wildtype AUXB1 0 | Wildtype AUXB1 +ACT D | Drug Resistant C5S32 0 | Drug Resistant C5S32 +ACT D |
|---|---|---|---|---|---|
| (A) | 1 μM | 0.90 | 0.77 | 0.96 | 0.67 |
|     | 10 μM | 0.69 | 0.47 | 0.41 | 0.07 |
| (B) | 1 μM | 1.00 | 1.00 | 1.00 | 1.00 |
|     | 10 μM | 1.00 | 0.86 | 0.86 | 0.49 |
| (C) | 1 μM | 0.91 | 0.52 | 0.30 | 0.42 |
|     | 10 μM | 0.73 | 0.04 | 0.05 | 0.03 |
| (D) | 1 μM | 0.78 | 0.61 | 1.00 | 0.93 |
|     | 10 μM | 0.79 | 0.50 | 1.00 | 0.66 |
| (E) | 1 μM | 0.74 | 0.67 | 0.90 | 0.92 |
|     | 10 μM | 0.65 | 0.37 | 0.76 | 0.29 |
| (F) | 1 μM | 0.93 | 0.82 | 0.61 | 0.71 |
|     | 10 μM | 0.96 | 0.52 | 0.15 | 0.15 |
| (G) | 1 μM | 0.97 | 0.48 | 0.56 | 0.93 |
|     | 10 μM | 0.96 | 0.18 | 0.27 | 0.11 |

EXAMPLE 7

In Vitro Cytotoxicity of Potentiating Agents in Human KB Epidermoid Carcinoma Cells The procedure for assaying the cytotoxicity of potentiating agents with human KB epidermoid carcinoma cells is essentially the same as the assay procedure described above for use with Chinese hamster ovary cells. In brief, KB 3-1 (wt) and KB V-1 (mdr) cells are plated at 500 cells/well in 96-well culture plates in Dulbecco's modified eagle medium, supplemented with 10% fetal calf serum. After 48 hours of incubation at 37° C., the media is changed and cells are treated with actinomycin D at 0.1 nM (3-1) or 20 nM (V-1). The test potentiating agent is introduced to one-half the untreated cultures and one-half the Act D treated cultures at 1 and 10 μM. After 96 hours of additional incubation at 37° C., 0.5 mg/ml MTT dye is added, the cells are incubated for three hours, after which the cells are dissolved in DMSO, and the absorbance is then read at 570 nm. The data is given in Table 2 below.

TABLE 2

In Vitro Cytotoxicity of Potentiating Agents in Human KB Epidermoid Carcinoma Cells

| Compound | Dose | Wildtype KB 3-1 0 | Wildtype KB 3-1 +ACT D | Drug Resistant KB V-1 0 | Drug Resistant KB V-1 +ACT D |
|---|---|---|---|---|---|
| (A) | 1 μM | 0.93 | 0.92 | 0.70 | 0.98 |
|     | 10 μM | 0.77 | 0.70 | 0.33 | 0.01 |
| (B) | 1 μM | 1.00 | 1.00 | 0.86 | 0.99 |
|     | 10 μM | 0.92 | 0.89 | 0.59 | 0.11 |
| (C) | 1 μM | 0.97 | 0.97 | 0.91 | 0.91 |
|     | 10 μM | 0.40 | 0.46 | 0.12 | 0.01 |
| (D) | 1 μM | 0.84 | 0.97 | 0.83 | 0.95 |
|     | 10 μM | 0.78 | 0.88 | 0.80 | 0.41 |
| (E) | 1 μM | 0.76 | 0.94 | 0.75 | 0.85 |
|     | 10 μM | 0.60 | 0.80 | 0.38 | 0.14 |
| (F) | 1 μM | 0.98 | 0.97 | 0.84 | 1.00 |
|     | 10 μM | 0.76 | 0.80 | 0.47 | 0.16 |
| (G) | 1 μM | 1.00 | 1.00 | 0.75 | 0.83 |
|     | 10 μM | 0.84 | 0.68 | 0.54 | 0.01 |

EXAMPLE 8

Formulations

In the formulations of this Example the active compound is a compound of Formula (I) described hereinbefore.

| (A) - Injectable | |
|---|---|
| Ingredient | Amount Per Ampoule |
| Active Compound | 1.0 mg |
| Water for Injections | 1.0 mL |

The finely ground active compound is dissolved in the water for injections. The solution is filtered and sterilized by autoclaving.

| (B) - Syrup | |
|---|---|
| Ingredient | Amount Per Ampoule |
| Active Compound | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Colouring | q.s. |
| Water | Q.S. to 5.0 mL |

Ethanol, sucrose, sodium benzoate, methylparaben, and flavouring are combined in 70% of the total batch quantity of water. Colouring and the active compound are dissolved in the remaining water, then the two solutions are mixed and clarified by filtration.

| (C) - Tablet | |
|---|---|
| Ingredient | Amount Per Tablet |
| Active Compound | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound is finely ground and intimately mixed with the powdered excipients lactose, corn starch, potato starch and magnesium stearate. The formulation is then compressed to afford a tablet weighing 126 mg.

| (D) - Capsule | |
|---|---|
| Ingredient | Amount Per Capsule |
| Active Compound | 1.0 mg |
| Lactose | 440.0 mg |
| Magnesium Stearate | 5.0 mg |

The finely ground active compound is mixed with the powdered excipients lactose and magnesium stearate and packed into gelatin capsules.

| (E) - Nasal Spray | |
|---|---|
| Ingredient | Amount Per 100.0 mL |
| Active Compound | 1 g |
| Sodium Chloride | 0.8 g |
| Preservative | 0.5 g |
| Purified Water | 100.0 mL |

The preservative is dissolved in warm purified water and after cooling to 25°-30° C. the sodium chloride and active compound are added. The pH is then adjusted to 5.5-6.5 and purified water is added to bring the final volume to 100.0 mL.

The foregoing Examples are illustrative of the present invention, and are not to be taken as restrictive thereof. The invention is defined by the following claims, with equivalents of the claims to be included therein.

That which is claimed is:

1. A method of combating multiple drug resistance of susceptible tumor cells in a subject in need of such treatment, comprising administering to the subject a compound, in an amount effective to combat multiple drug resistance of tumor cells sensitive to said compound, wherein said compound is selected from the group consisting of

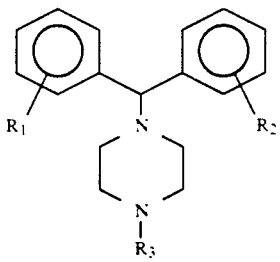

wherein:
$R_1$ is halogen;
$R_2$ is selected from the class consisting of hydrogen, halogen, $C_{1-4}$ alkoxy, $-OCH_2C_6H_5$, and $-CH=CHCO_2R$, wherein R is $C_{1-4}$ alkyl; and
$R_3$ is selected from the class consisting of $C_{1-4}$ alkyl, $-CH_2CH=CH_2$, and $-CH_2C_6H_3$;
and the pharmaceutically acceptable salts thereof.

2. A method according to claim 1, wherein $R_1$ is 4-chloro, $R_2$ is 3-benzyloxy, and $R_3$ is methyl.

3. A method according to claim 1, wherein said compound is 1-(3-Bromo-4'-chlorobenzhydryl)-4-methylpiperazine dihydrochloride.

4. A method according to claim 1, wherein said compound is (E)-Ethyl 3-(4-chloro-α-(4-methyl-1-piperazinyl)-benzyl)cinnamate dihydrochloride.

5. A method according to claim 1, wherein said compound is 1-(3-Benzyloxy-4'-chlorobenzhydryl)-4-methylpiperazine dihydrochloride.

6. A method according to claim 1, wherein said compound is 1-(3-Benzyloxy-4'-chlorobenzhydryl)-4-(3-methylbenzyl)piperazine dihydrochloride.

7. A method according to claim 1, wherein said compound is 1-(2-Bromo-4'-chlorobenzhydryl)-4-methylpiperazine dihydrochloride.

8. A method according to claim 1, wherein said compound is 1-(α(4-Bromophenyl)-3-methoxybenzyl)-4-methylpiperazine dihydrochloride.

9. A method according to claim 1, wherein said compound is 1-4-allylpiperazine dihydrochloride.

10. A method according to claim 1, wherein said tumor cells are adenocarcinoma cells.

* * * * *

UNITED STATES PATENT AND TRADEMARK OFFICE
CERTIFICATE OF CORRECTION

PATENT NO. : 5,124,330
DATED : 23 June 1992
INVENTOR(S) : Ann C. Kine

It is certified that error appears in the above-identified patent and that said Letters Patent is hereby corrected as shown below:

Column 1, line 43, please add after Chemotherapy --8--.

Column 8, line 3, please change "00 ml" to --300 ml--.

Column 10, line 64, please change "0.0µM" to --0.01µM--.

Column 14, line 16, please change "OCH$_2$C$_6$ H$_{51}$" to --OCH$_2$C$_6$ H$_5$--.

Column 14, line 19, please change "CH$_2$C$_6$H$_3$" to --CH$_2$C$_6$H$_4$CH$_3$--.

Column 14, line 43, Claim 3, please change "-4-" to --[α-(4-chlorophenyl)-3-methoxybenzyl]-4- --.

Signed and Sealed this

Fourteenth Day of September, 1993

Attest:

BRUCE LEHMAN

Attesting Officer   Commissioner of Patents and Trademarks